(12) United States Patent
Bluteau

(10) Patent No.: US 6,573,837 B2
(45) Date of Patent: Jun. 3, 2003

(54) SENSOR DEVICE AND AN ANALYZING DEVICE SPECIFICALLY ADAPTED TO BE USED IN CONJUNCTION WITH DIAPERS FOR INCONTINENT PATIENTS

(76) Inventor: Yves Bluteau, 38, Lauzon, Boisbriand, Quebec (CA), J7E 4H5

( * ) Notice: Subject to any disclaimer, the term of this patent is extended or adjusted under 35 U.S.C. 154(b) by 0 days.

(21) Appl. No.: 09/981,699

(22) Filed: Oct. 18, 2001

(65) Prior Publication Data

US 2003/0011479 A1 Jan. 16, 2003

(30) Foreign Application Priority Data

Jul. 13, 2001 (CA) .............................................. 2353906

(51) Int. Cl.⁷ .............................................. G08B 21/00
(52) U.S. Cl. ..................... 340/604; 340/573.5; 340/605
(58) Field of Search .............................. 340/604, 573.5, 340/605, 603

(56) References Cited

U.S. PATENT DOCUMENTS

| | | | | |
|---|---|---|---|---|
| 5,392,032 A | * | 2/1995 | Kline et al. ................... | 340/604 |
| 5,486,806 A | * | 1/1996 | Firari et al. ................... | 340/426 |
| 5,557,255 A | * | 9/1996 | Adams et al. ............... | 340/426 |
| 5,696,408 A | * | 12/1997 | Man ........................... | 307/10.3 |
| 6,097,297 A | * | 8/2000 | Fard ............................ | 340/604 |
| 6,200,250 B1 | * | 3/2001 | Janszen ....................... | 493/383 |
| 6,407,308 B1 | * | 6/2002 | Roe et al. .................... | 604/361 |

\* cited by examiner

Primary Examiner—Daniel J. Wu
Assistant Examiner—Phung Nguyen

(57) ABSTRACT

Sensor device and an analyzing device specifically adapted to be used in conjunction with diapers for incontinent patients, is adapted to transmit the sensed data to a remote analyzing system, the monitoring can be performed with the patient in various situations and positions, the sensor is adapted to be coupled to a computer system which can monitor and analyse the various data so as to manipulate the information and extract various types of valuable data, the sensor is adapted to sense both variations in moisture and in temperature as well as other physiological data such as the glucose level of the urine from the patient, or other biochemical data emanating from the patient.

3 Claims, 4 Drawing Sheets

SENSOR DEVICE AND AN ANALYZING DEVICE SPECIFICALLY ADAPTED TO BE USED IN CONJUNCTION WITH DIAPERS FOR INCONTINENT PATIENTS

BACKGROUND OF THE INVENTION

1. Field of the Invention

The present invention relates to the field of sensor devices and is particularly concerned with a sensor device and an analyzing device specifically adapted to be used in conjunction with diapers for incontinent patients detecting the presence of urine or fecal matter, and other physiological or biochemical data emanating from the patient.

2. Description of the Related Art

The demographical trend towards an older population has created a situation wherein a relatively large number of individuals suffers from incontinence. Furthermore, some of these patients have lost at least a portion of their cognitive functions. Such patients are often found in institutions where they are left alone for a relatively long period of time.

Accordingly, some of these patients wearing adult diapers are left for a relatively long period of time with the diaper soiled and unchanged.

Indeed, it is logistically relatively difficult for the personnel of such institutions to monitor the state of the patient's diaper on a continuous basis.

A search amongst the prior art has revealed one system adapted to monitor the state of a patient lying in a bed. The device consists in a sheet of material having an electric sensor which sounds off an alarm when moisture is detected. However, the device must be embedded into a bed sheet and thus is not functional when the patient is not lying in the bed.

SUMMARY OF THE INVENTION

Accordingly, it is an object of the present invention to provide an improved sensor device in conjunction with diapers for incontinent patients.

Advantages of the present invention include the fact that the sensor device in accordance with the present invention can be readily mounted to conventional diapers so that the monitoring can be ferformed with the patient in various situations and positions.

Another advantage of the present invention resides in the fact that the sensor device in accordance with the present invention is adapted to transmit the sensed data to a remote analyzing system.

A further advantage of the present invention resides in the fact that the sensor device in accordance with the present invention is adapted to be coupled to a computer system that can monitor and analyse the various data so as to manipulate the information and extract various types of valuable data.

A still further advantage of the present invention resides in the fact that the sensor device in accordance with the present invention is adapted to sense both variations in moisture and in temperature as well as other physiological data such as the glucose level of the urine from the patient or other biochemical data emanating from the patient.

BRIEF DESCRIPTION OF THE SEVERAL VIEWS OF THE DRAWING(S)

DETAILED DESCRIPTION OF THE INVENTION

Figure 1:
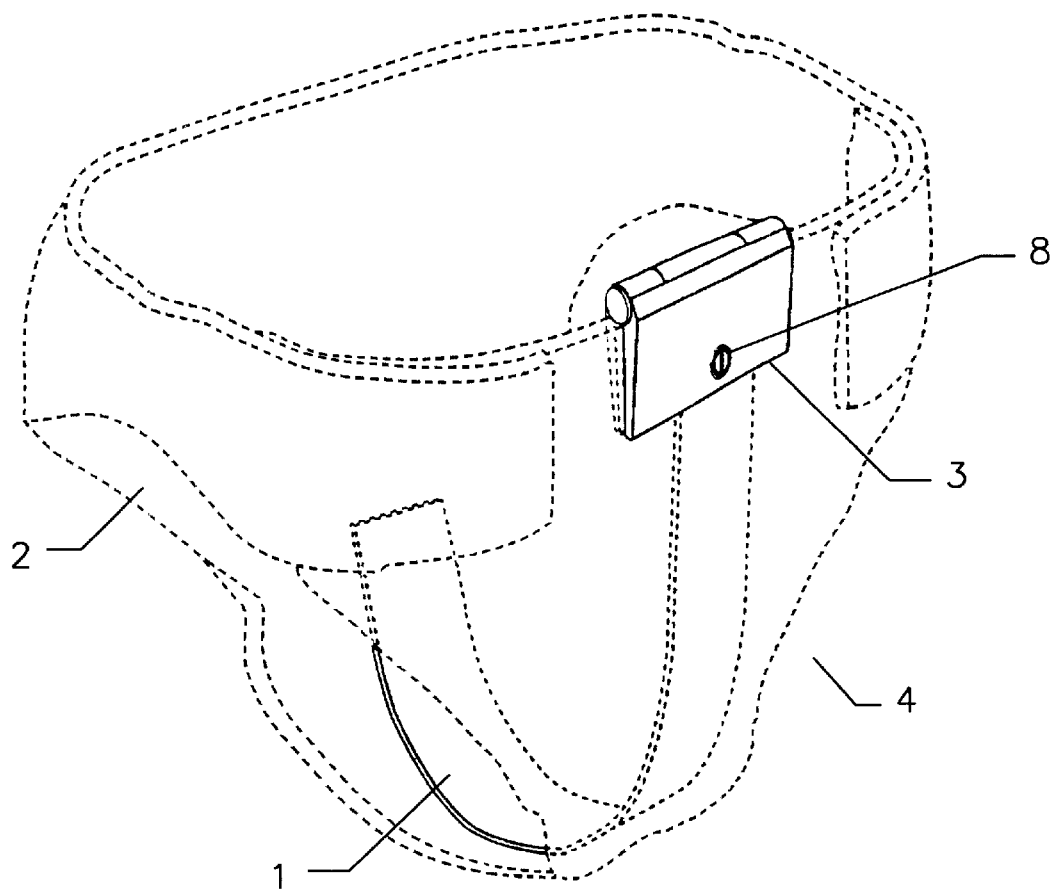
FIG. 1 is a perspective view showing a sensor device in accordance with an embodiment of the present invention mounted inwardly from a conventional diaper shown in phantom lines.

Referring to FIG. 1, there is shown a sensor device (4) in accordance with an embodiment of the present invention. The sensor device (4) includes a sensing strip (1), a transmitting component (3) and a releasable locking means (8).

Figure 3:
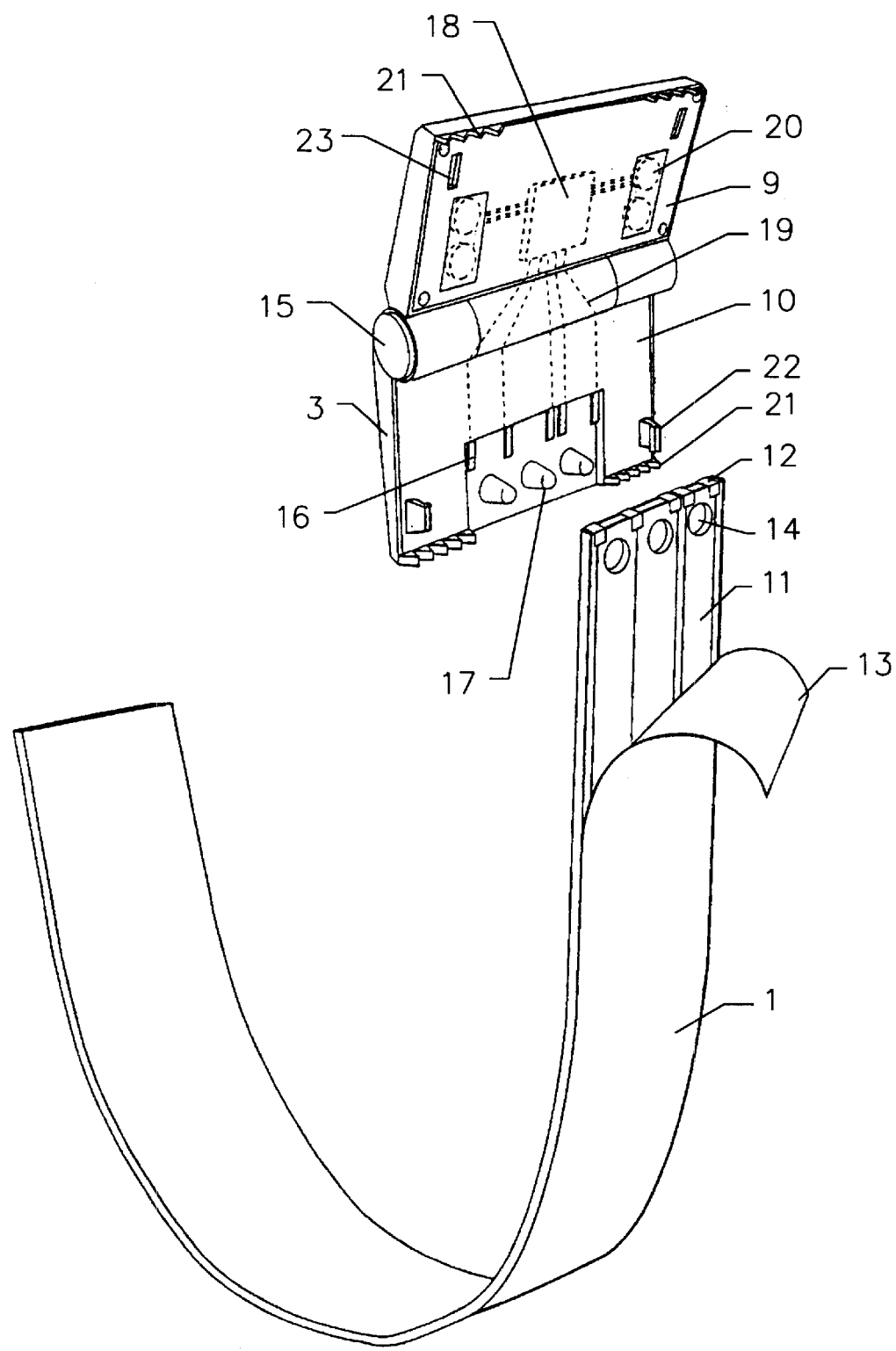
FIG. 3 is a perspective and partly exploded view, showing a sensor device in accordance with an embodiment of the present invention.
Figure 4:
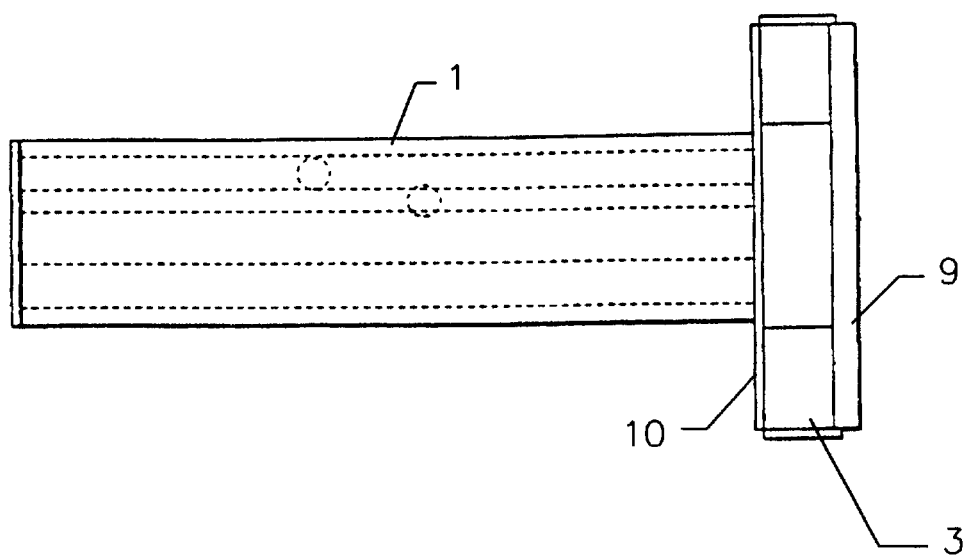
FIG. 4 is a top view showing a sensor device in accordance with an embodiment of the present invention.

As illustrated in FIG. 3, the sensing strip (1) is typically made of a set of juxtaposed elongated and relatively thin metallic strips (11). A set of connecting clips (12) is positioned in an overlapping configuration at one terminal end of the metallic strips (11). The connecting clips (12) are adapted to act as transmitting contacts for transmitting the electrical data emanating from the metallic strips (11) to the transmitting component (3), as will be hereinafter described.

The metallic strips (11) are preferably coated with an adhesive material or covered by an adhesive strip. The adhesive material or strip covering the metallic strips (11) is itself covered by a protective strip of material (13) releasably secured to the metallic strips (11). The strip of material (13) is adapted to act as a peal-off protective strip allowing the sensing strip (1) to be conveniently stored and carried when in place and once removed allowing the metallic strips (11) to be adhesively and releasably secured to the interior surface of a diaper (2), as illustrated in FIG. 1.

A set of coupling apertures (14) extends through the metallic strips (11) adjacent one of the longitudinal ends of the sensing strip (1). The coupling apertures (14) are adapted to be used to connect the sensing strip (1) to the metallic strips (11).

The transmitting component (3) typically has a generally parallelepiped-shaped general configuration. The transmitting component (3) typically consists in a first panel (9) hingely connected to a second panel (10) by a hinge component (15). The second panel (10) is provided with a strip receiving recess formed therein. A set of connecting prongs (16) extends integrally from the hinge component (15). The prongs (17) are adapted to be slidably inserted into the coupling apertures (14) of the sensing strip (1) in order to facilitate the proper alignment of the terminal end of the sensing strip (1) inside the hinge component (15).

A set of contact prongs (16) is embedded in the second panel (10) and extends into the hinge component (15). The contact prongs (16) are positioned so as to be in register with the connecting clips (12) of the sensing strip (1). Each connecting clip (12) is thus adapted to be put in contact with a corresponding contact prong (16) when the terminal end of the sensing strip (1) is positioned inside the hinge component (15). The connecting clips (12) is thus adapted to transmit the electrical data signal from the sensing strip (1) to the contact prongs (16).

The contact prongs (16) are electrically coupled to a surface mount microchip (18) embedded in the first panel (9) by a set of connecting wires (19). A battery source typically consisting of a set of lithium flat cells (20) is also enclosed in the first panel (9). The distal peripheral edges of both the second panel (10) and the first panel (9) are provided with a set of gripping teeth (21). The gripping teeth (21) are adapted to cooperate for fixing the transmitting component (3) to the peripheral edge of the diaper (2) when the first panel (9) and the second panel (10) are pivoted towards one another.

A set of resilient gripping tongues (22) extends from the second panel (10). A corresponding pair of tongue receiving slots (23) is formed in the first panel (9). The gripping tongues (22) are adapted to be snappingly inserted into the tongue receiving slots (23) in order to releasably secure the transmitting component (3) in an overriding relationship over the peripheral edge of the diaper (2).

As illustrated more specifically in FIG. 1, a releasable locking means (8) is adapted to be optionally used for locking the transmitting component (3) to the diaper (2) in order to prevent the unwanted removal of the transmitting component (3) from the diaper (2) for example when the patient is demential or otherwise uncooperative. The locking means (8) can take various conventional forms such as an electromagnetic lock, a mechanical lock or the like.

The surface microchip (18) includes a microprocessor adapted to analyze the various electrical data emanating from the metallic strips (11) in the form of current or potential variation between the various metallic alloys from which the metallic strips (11) are made. The microchip (18) is preferably programmed so as to compute and store the data emanating from the sensing strip (1). Typically, the microchip (18) is adapted to store the time of day at which the diaper was soiled by biological fluids. The microchip (18) is also adapted to analyze the biochemical properties of the biochemical fluids that are put into contact with the metallic strips (11) in order for example to determine the sugar level in the urine of the diabetic patients.

Figure 2:
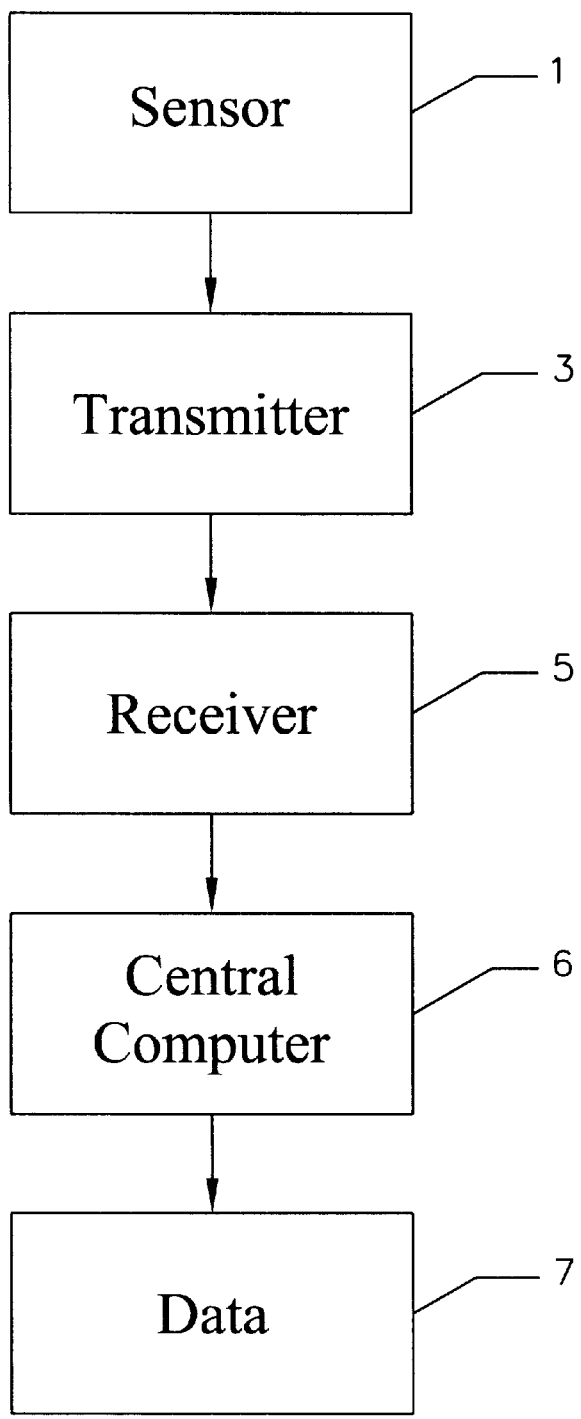
FIG. 2 is a schematic diagram showing a sensor sending a signal to a remote receiver which sends a signal to a central computer system.

The data emanating from the metallic strips (11) and sent to the microchip (18) is also adapted to be transmitted to a receiver schematically illustrated and designated by the reference numeral (5) in FIG. 2. The data (7) sent by the transmitter (3) to the receiver (5) could be in various forms such as a numeric form and could be sent by radiowaves, microwaves or any other suitable medium. The receiver (5) is adapted to be connected to a central computer system schematically illustrated and designated by the reference numeral (6) in FIG. 2.

The data (7) emanating from the sensor device (4) could be stored by the central computer system (6) for a number of patients. A cyclic pattern for each patient and each department could thus be elaborated taking into account the record of diaper soiling collected by the various sensor devices (4) for various patients. For a given patient, the collection of data (7) could lead to the establishment of a time pattern at which a given patient typically wets the diaper (2). This information can prove to be very valuable for the personnel allowing the latter to attend to a given patient recording to the predicted time of need.

The sensor devices (4) could also be used in order to monitor the time period between the soiling of the diaper and the changing of the latter by the personnel in order to evaluate the efficiency of the personnel. Also, the data (7) could allow to optimize the work of the personnel by grouping patients according to their estimate time of need. The various types of data (7) hereinabove mentioned are only given as example and should not limit the scope of the invention since various other biological data such as the temperature of the patient, the loss of weight, the biochemical contents of the urine or fecal matter, or any suitable data could be monitored by using the sensor device in accordance with an embodiment of the present invention without departing from the scope of the present invention.

The sensing strip (1) could be manufactured using conventional manufacturing process in which a continuous strip is processes in order to cut down on manufacturing time and cost.

The embodiments of the invention for which an exclusive property or privilege is claimed, are defined as follows:

1. A sensor device and an analyzing device adapted to be used in conjunction with conventional diapers for incontinent patients, detecting the presence of urine or fecal matter, and other physiological or biochemical data emanating from the patient, wherein said sensor device comprises a sensing strip, a transmitting component and a releasable locking means:

(a) the sensing strip is made of a set of juxtaposed elongated and relatively thin metallic strips, wherein the connecting clips are positioned in an overlapping configuration at one terminal end of said metallic strips, and said connecting clips are adapted to act as transmitting contacts for transmitting the electrical data emanating from said metallic strips to said transmitting component;

(b) the metallic strips me preferably coated with an adhesive material or covered by an adhesive strip, the adhesive material or strip covering said metallic strips is itself covered by a protective strip of material releasably secured to said metallic strips, wherein said strip of material is adapted to act as a peal-off protective strip allowing to said sensing strip to be conveniently stored and carried when in place and once removed allowing to said metallic strips to be adhesively and releasably secured to the interior surface of the diaper, a set of coupling apertures extends through said metallic strips adjacent one of the longitudinal ends of said sensing strip, and said coupling apertures are adapted to be used to connect said sensing strip to said metallic strips;

(c) the transmitting component has generally a parallelepiped-shaped general configuration comprising a first panel hingely connected to a second panel by a hinge component, wherein said second panel is provided with a strip receiving recess formed therein, a set of connecting prongs extends integrally from said hinge component and said prongs are adapted to be slidably inserted into said coupling apertures of said sensing strip in order to facilitate the proper alignment of the terminal end of said sensing strip inside said binge component, a set of contact prongs is embedded in said second panel and extends into said hinge component and said contact prongs are positioned so as to be in register with said connecting clips of said sensing strip, wherein each said connecting clip is adapted to be put in contact with said corresponding contact prong when the terminal end of said sensing strip is positioned inside said hinge component, and wherein said connecting clips are adapted to transmit the electrical data signal from said sensing strip to said contact prongs;

(d) the contact prongs are electrically coupled to a surface mount microchip embedded in said first panel by a set of connecting wires, a battery source constituted of a set of lithium flat cells is enclosed in said first panel, the distal peripheral edges of both the second panel and the first panel are provided with a set of gripping teeth, wherein said gripping teeth are adapted to cooperate for fixing said transmitting component to said peripheral edge of the diaper when said first panel and said second panel are pivoted towards one another, and a set of resilient gripping tongues extends from said second panel, a corresponding pair of tongue receiving slots is formed in said first panel, and said gripping tongues are adapted to be snappingly inserted into said tongue receiving slots in order to releasably secure said transmitting component in an overriding relationship over said peripheral edge of the diaper;

(e) a releasable locking means is adapted to be used for locking said transmitting component to the diaper in order to prevent the unwanted removal of said transmitting component from the diaper when the patient is demential or otherwise uncooperative, and said locking means can take various conventional forms including an electromagnetic look or a mechanical lock;

(f) the surface microchip includes a microprocessor adapted to analyze the various electrical data emanating from said metallic strips in the form of current or potential variation between the various metallic alloys from which said metallic strips are made, and said microchip allows to compute and store the data emanating from said sensing strip, the time of day at which the diaper was soiled by biological fluids, and to analyze the biochemical properties of the biochemical fluids that are put into contact with said metallic strips in order to determine the sugar level in the urine of the diabetic patients; and (g) the data emanating from said metallic strips and sent to said microchip is adapted to be transmitted to a receiver, said data sent by said transmitter to said receiver being one of various forms including a numeric form and being sent by one of radiowaves, microwaves or any other suitable medium, and wherein said receiver is adapted to be connected to a central computer system.

2. The sensor device, according to claim 1, wherein said data emanating from said sensor device are stored by said central computer system for a number of patients, a cyclic pattern for each patient and each department is elaborated taking into account the record of diaper soiling collected by said various sensor devices for various patients, for a given patient, the collection of data leads to the establishment of a time pattern at which a given patient wets the diaper, and this information can prove to be very valuable for the personnel allowing the latter to attend to a given patient recording to the predicted time of need.

3. The sensor device according to claim 1, wherein said sensor devices are used in order to monitor the time period between the soiling of the diaper and the changing of the latter by the personnel in order to evaluate the efficiency of the personnel, the data allows to optimize the work of the personnel by grouping patients according to their estimate time of need, the biological data comprising the temperature of the patient, the loss of weight the biochemical contents of the urine or fecal matter, or any suitable data are monitored by using said sensor device.

* * * * *